United States Patent [19]
Milosevic et al.

[11] Patent Number: 5,214,286
[45] Date of Patent: May 25, 1993

[54] HORIZONTAL MULTIPLE INTERNAL REFLECTION ACCESSORY FOR INTERNAL REFLECTION SPECTROSCOPY

[75] Inventors: Milan Milosevic, Fishkill; Nicolas J. Harrick, Ossining, both of N.Y.

[73] Assignee: Harrick Scientific Corporation, Ossining, N.Y.

[21] Appl. No.: 895,019

[22] Filed: Jun. 8, 1992

[51] Int. Cl.⁵ .............................................. G01J 3/42
[52] U.S. Cl. ................................... 250/339; 250/341; 250/353; 356/244; 356/326; 356/440
[58] Field of Search ...................... 250/339, 341, 353; 356/244, 326, 440

[56] References Cited
U.S. PATENT DOCUMENTS
4,175,864 11/1979 Gilby ................................... 356/244

Primary Examiner—Carolyn E. Fields

[57] ABSTRACT

The multiple internal reflection accessories for internal reflection spectrometry described here utilizes a novel approach to match the round beam size and shape from a conventional FT-IR spectrometer to the typical rectangular IRE aperture. Its transfer optics distort the beam entering and exiting the IRE so that the cross-section of the beam is matched to that of the standard rectangular aperture of the IRE. This configuration reduces energy losses, eliminates the need to aluminize the edges of the crystal, and reduces spurious peaks from the adhesive or O-rings used to conventionally mount the crystal.

16 Claims, 11 Drawing Sheets

FIG 6 - PRIOR ART

HORIZONTAL MULTIPLE INTERNAL REFLECTION ACCESSORY FOR INTERNAL REFLECTION SPECTROSCOPY

RELATED APPLICATION

Copending application, Ser. No. 07/831,529, filed in our joint names on Feb. 5, 1992, of which the present case is a continuation-in-part.

BACKGROUND OF THE INVENTION

This invention relates to internal reflectance spectroscopic analysis, and in particular to an accessory employing an internal reflection element with a flat sampling surface portion for use with such a technique for the spectroscopic analysis of various samples.

Optical spectroscopy is one of the most powerful and widely employed analytical techniques currently in use. There is a universal demand for a non-destructive, spectroscopic probe of samples of all sizes and in various states, such as powder, solid or liquid. Internal reflectance spectrometry is widely used for this purpose. Since the sample is simply placed in optical contact with a prism, internal reflectance requires little or no sample preparation. In a typical laboratory or factory application, the user purchases an internal reflection accessory which is installed in the sampling compartment of the user's optical spectrometer. As background material, see, for example, "Internal Reflection Spectroscopy", available from Harrick Scientific Corp., and U.S. Pat. No. 4,602,869, the contents of which are herein incorporated by reference. The latter describes an IR accessory, primarily for analysis of liquid samples, having a convenient horizontal sampling surface. However, multiple interactions to enhance the signal strength are not possible in this accessory.

Mirrors (ellipsoids, toroids, paraboloid and spherical mirrors) in attachments or accessories are widely used for IR-VIS-UV spectrometers. These mirrors must be used in an off-axis mode in order to have adequate space to place samples with the accessory between the mirrors to record spectra of the samples. The accessories may be designed for various spectroscopic techniques, e.g., transmission, internal reflection, external reflection, diffuse reflection, etc. Ellipsoids, toroids and paraboloids can be fabricated to produce good imaging for off-axis operation. Spherical mirrors can be fabricated at lower costs and yield good imaging for on-axis or small off-axis angles operation, for example, 5°-10° or less. For large off-axis angles, for example, exceeding 20°, serious astigmatism occurs. This astigmatism causes problems in, e.g., re-imaging the light source on the instrument detector element and therefore reduces the sensitivity of the system.

Originally, internal reflectance accessories were designed for use with dispersive spectrometers. These accessories directed the beam to and from the IR elements (IREs). These IREs were typically parallelepipeds or trapezoids and had apertures slightly larger than the slit image of the spectrometer. This produced highly efficient multiple reflection IR accessories. When FT-IR spectrometers began to replace the dispersive instruments, many of the accessories designed for dispersive spectrometers continued to be used. FT-IR spectrometers, however, have beams with round cross-sections and hence do not match the rectangular aperture of the standard IRE. This mismatch results in energy losses that lower the throughput of the IR accessories and reduce the signal-to-noise (S/N) ratio in the resulting spectra.

Two general approaches have been taken to circumvent this dilemma: redesigning the IRE to match its aperture to the FT-IR beam or reshaping the FT-IR beam to match the IRE. In the former category, IREs with square and round apertures have been designed in an attempt to reduce the resulting energy losses. Both configurations have their limitations. The IREs with square cross-sections are designed with apertures slightly larger than the focused FT-IR beam. Like the standard IREs, they have flat sampling surfaces which are easily polished to an optical quality finish and provide scattering-free total internal reflection. These flat sampling surfaces can be oriented horizontally and exposed and are thus ideal for mounting the sample and for applying pressure to obtain optimum contact between the sample and the IRE. However, square cross-sectioned IREs have fewer reflections and hence lower S/N ratios than the traditionally shaped IREs of the same height and length. Use of a longer IRE can increase the S/N ratio, but there is a practical limit to the length based on the width of the sample compartment, the fragility of the IRE, and the ability to achieve good optical contact between the IRE and the sample.

Alternatively, rod-shaped IREs require more expensive transfer optics to direct the entering and exiting beams. These transfer optics are typically difficult to align and result in low throughput. Typically, the throughput is even lower than that of accessories which use rectangular IREs and do nothing to overcome the resulting energy losses. In addition, rods do not produce a well-defined incident angle due to their curved sampling surfaces. These curved surfaces are difficult to polish to a high quality optical finish, resulting in increased scattering losses relative to the standard rectangular IREs. The curved sampling surfaces also limit the types of samples that can be examined. Since solids and powders cannot be clamped onto the crystal, rod IREs are only utilized for liquid sampling.

Internal reflectance beam condensers represent still another approach to solving the FT-IR beam-IRE aperture incompatibility problem. Beam condensers focus and condense the round FT-IR beam into the IRE aperture. This produces a beam that fits within the entrance aperture of the IRE, but it expands within the IRE and completely fills the exit aperture. The beam exiting the IRE has a rectangular cross-section with a width comparable to the diameter of the condensed FT-IR beam and a height several times larger. This elongated beam is directed to the detection optics of the spectrometer. Thus, some fraction of the rectangular beam will not strike the detector. This results in energy losses, low throughput, and a less than optimal S/N ratio.

Harrick Scientific has offered for sale for use in sampling compartments with center focussing optics, a horizontal IRS attachment (Model HRA) for applications requiring an exposed sampling surface. This uses a trapezoidal IRE and plane mirrors to direct the beam to the IRE entrance aperture. But with a round FT-IR beam, light throughput is low and sensitivity suffers.

SUMMARY OF THE INVENTION

The chief object of the invention is an internal reflection accessory for multiple internal reflection spectrophotometry that provides a better match between the beam size and shape generated by an optical spectrometer and the IRE aperture, particularly for round beams as are generated by an FT-IR spectrometer.

In accordance with one aspect of the invention, the accessory comprises at least a first spherical mirror located in the path of but off the axis of the round radiation beam generated by the spectrometer and entering its sample compartment. The off-axis spherical mirror directs the beam to the entrance aperture of an IRE having the typical preferred parallelepiped or trapezoidal shape. The astigmatism inherent in the off-axis spherical optical geometry distorts the beam shape, generating two, spaced, generally oval-shaped images transverse to one another, referred to as primary and secondary images. The location of the IRE relative to the first spherical mirror, the angle of incidence on the mirror, and the spherical mirror dimensions are chosen such that the primary image of the spherical mirror substantially coincides with the entrance aperture of the IRE, and the secondary image of the spherical mirror is located approximately at the center of the IRE.

The result is that the beam shape at the IRE entrance aperture is very closely matched to the normal rectangular entrance aperture of the IRE. Moreover, an additional benefit is that the beam shape changes inside the IRE, and, in particular, contracts in the plane of the IRE, with the consequence that very few reflections occur at the IRE edges, which thus are rendered insensitive to contact with foreign materials, such as cements, O-ring seals, supports, etc. The result is that the IRE is easier to mount in the accessory with little risk of spurious spectra due to interaction of the beam with such foreign materials at the mount locations. The ends of the IRE plates can either be shielded by metal foil if used as apertures, or instead of using the plate ends as apertures small prisms can be optically contacted near the ends to inject and extract the beam thereby leaving the ends free for sealing via adhesives or O-rings. This latter construction can simplify sealing the IRE plate to its plate holder which offers certain advantages when carrying out analysis of liquid samples.

A further feature of the invention is the use of a second spherical mirror downstream of the IRE. In this case also, the second spherical mirror is off the axis of the IRE and is positioned and dimensioned such that its secondary image is located substantially at the IRE center, i.e., it coincides substantially with the secondary image of the first spherical mirror, and its primary image is located substantially at the exit aperture of the IRE. The result is that the beam after reflection from the second spherical mirror will be generally oval in cross-section so that it now substantially matches the round detection optics of a typical FT-IR spectrometer, reducing energy losses.

The accessory according to the invention not only performs as indicated above, and increases light throughput by at least 30%, but also is capable of low-cost manufacture, is simple to operate, and can also be adapted for external or in-line diffuse reflectance for some samples.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

DETAILED DESCRIPTION OF THE PREFERRED EMBODIMENTS

Figure 1:
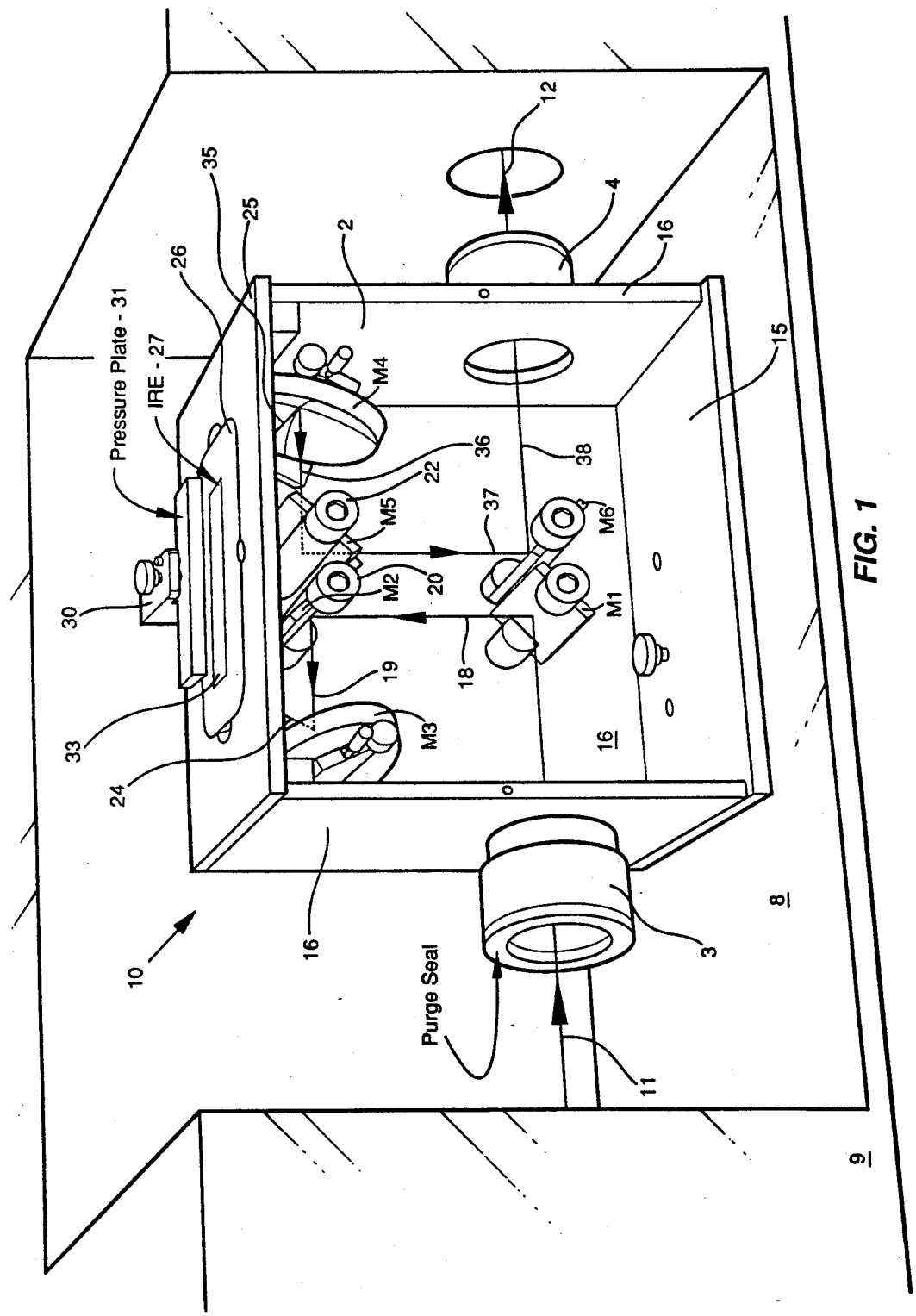
FIG. 1 is a perspective view of one form of accessory device according to the invention with a side of its enclosure removed to show its interior.

One form of an accessory device 10 according to the invention is illustrated in FIG. 1. As described in the related application, Ser. No. 831,529, now U.S. Pat. No. 5,177,561, it comprises an enclosure 2 forming a sealed interior for a purging medium. A window-sealed inlet 3 allows a radiation beam 11 to enter the enclosure, and a window-sealed outlet 4 allows a radiation beam 12 to exit the enclosure. The purging medium can be provided via a pipe (not shown). See the reference related case for a more elaborate description of the purging arrangement. As is conventional for such accessories 10, it is adapted to fit within the sampling compartment 8 of a conventional FT-IR optical spectrometer 9. The latter typically provides a radiation beam with a round cross-section in the infrared, visible, or ultraviolet portions of the spectrum. While the analyzer of the invention can, in principle, be used with visible or ultraviolet radiation, the most common use is with infrared (IR) radiation, and the invention will be described in the latter application.

The radiation beam provided by the spectrometer 9, which beam is designated 11, is, in use, typically swept across a range of wavelengths to produce the conventional spectra which plot sample absorbance as a function of wavelength or wavenumber. The beam 11 typically converges to a small area in the sampling compartment 8 and then diverges to form an exiting beam which is received by the spectrometer and detected by the spectrometer detector element, typically with a rectangular aperture, and the resultant electrical signal processed in the normal manner. If the beam has interacted with a sample, the beam intensity is modulated at wavelengths characteristic of the sample structure. The typical accessory must intercept the entrance beam 11, redirect it to the sample, and then restore the beam leaving the sample to the path 12 it would have followed if the accessory were not present. By proper adjustment of the optical path lengths within the accessory, using proper optical elements, the original focussing conditions can be maintained.

In this case, the accessory 10 is designed for internal reflection spectroscopy using an IRE crystal plate 27 mounted in the top wall 25 of a sealed enclosure 2. The sample (not shown) is placed on the exposed top sampling surface 33 of the IRE, and pressure applied via a pressure plate 31 cantilevered by a support 30 over the IRE plate. The beam enters via a sealed window 3 and is conveyed by suitable optics M1, M2 and M3 to enter the IRE 27 at its left bevelled edge. The beam propagates in the well known manner down the IRE, interacting with the sample on its surface, exits at the IRE opposite bevel end, and is then directed by optics M4, M5, and M6 out a sealed exit window 4. This accessory 10 sits in an open sample compartment in the manner shown in FIG. 1, and can be separately, independently purged via a purge inlet fitting. Alternatively, the windows 3, 4 can be opened, and the enclosure coupled to the spectrometer ports by means of an adaptor in a dependent purging mode as described in the related application.

Referring back to FIG. 1, the accessory comprises a base member 15 with side walls 16 (only three of which are shown) for supporting the various optical and physical elements. The optical elements include first and second plane mirrors M1, M2, which direct the entrance beam 11 along a path designated 18, 19 toward a first spherical mirror M3 located off the optical axis of the incident beam. The mirror M2 comprises a support 20 for a plane mirror 21, with means 22 for angular and vertical positioning of the mirror 21.

The radiation beam 24 reflected from the spherical mirror M3 is directed toward a structure which supports the internal reflection element (IRE) 27. The support structure comprises a plate 26 with an aperture in which the IRE 27 is seated, the plate in turn being supported by the top wall 25 of the enclosure. The lower portion of the IRE (not shown in FIG. 1) is suspended inside the enclosure and its left and right edges are bevelled and exposed to form the rectangular entrance and exit apertures of the IRE. The pressure applying mechanism 30 comprises a plate-like member 31 which is mounted for vertical movement by a user by means of the mechanism shown.

Figure 4:
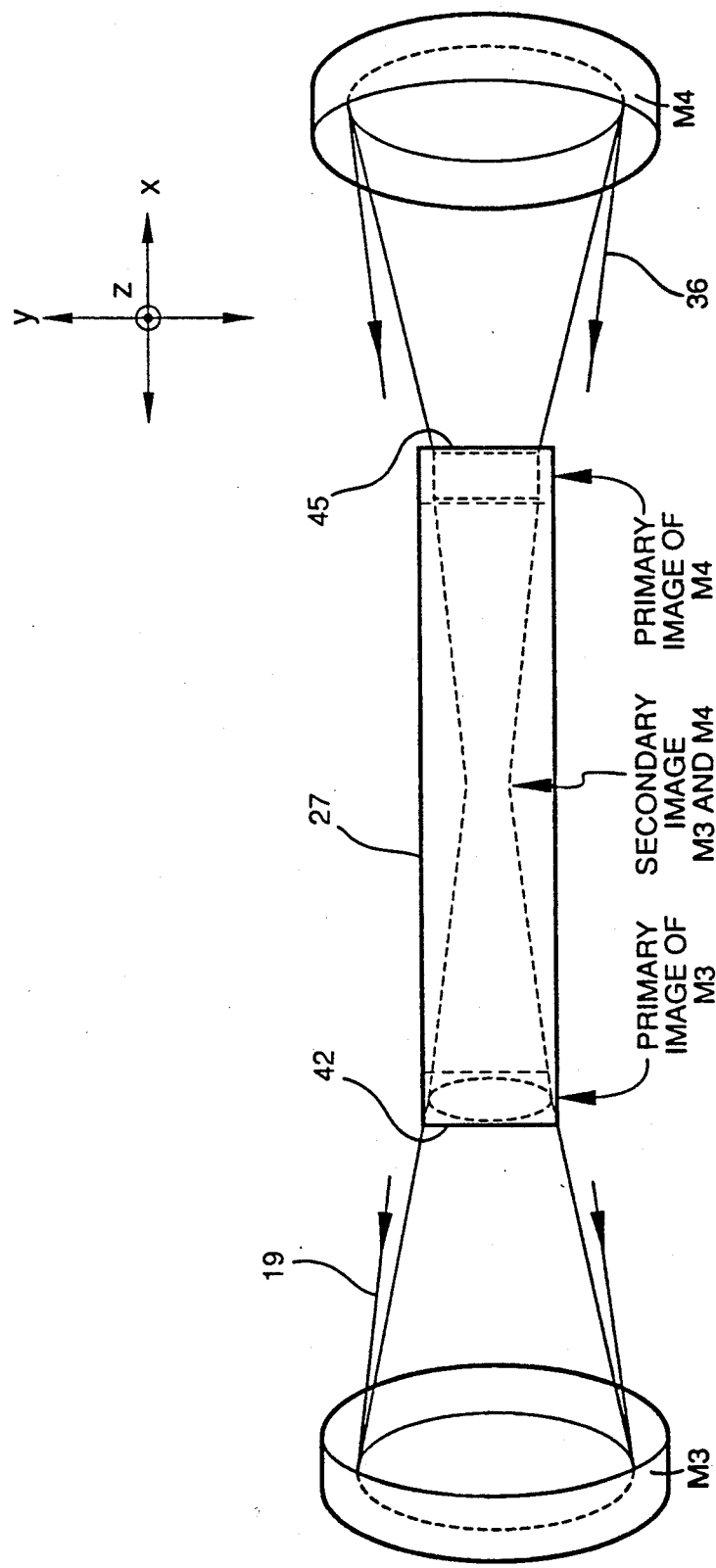
FIGS. 4 and 5 are, respectively, a view from the top and a perspective view of the optical paths of the accessory device of FIG. 1 showing the optical geometry of the various images formed in the system.
Figure 5:
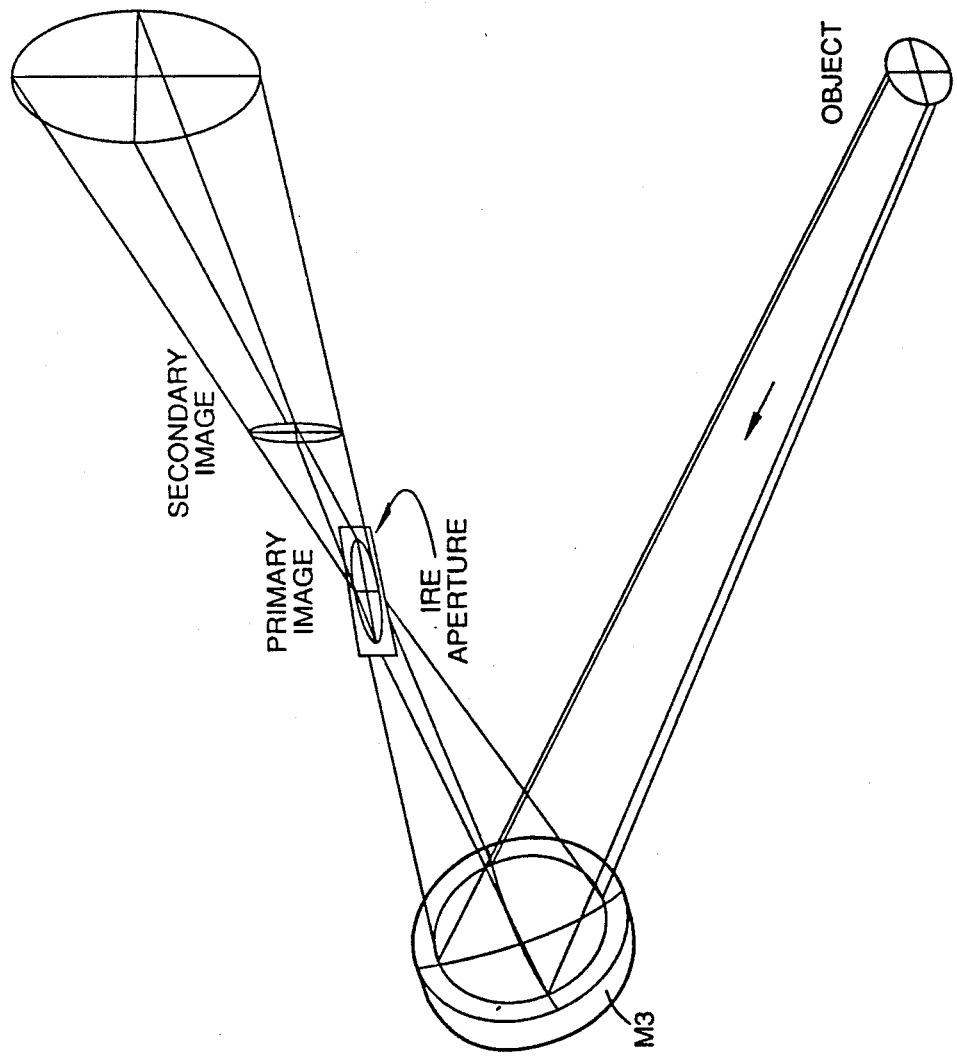
Figure 6:
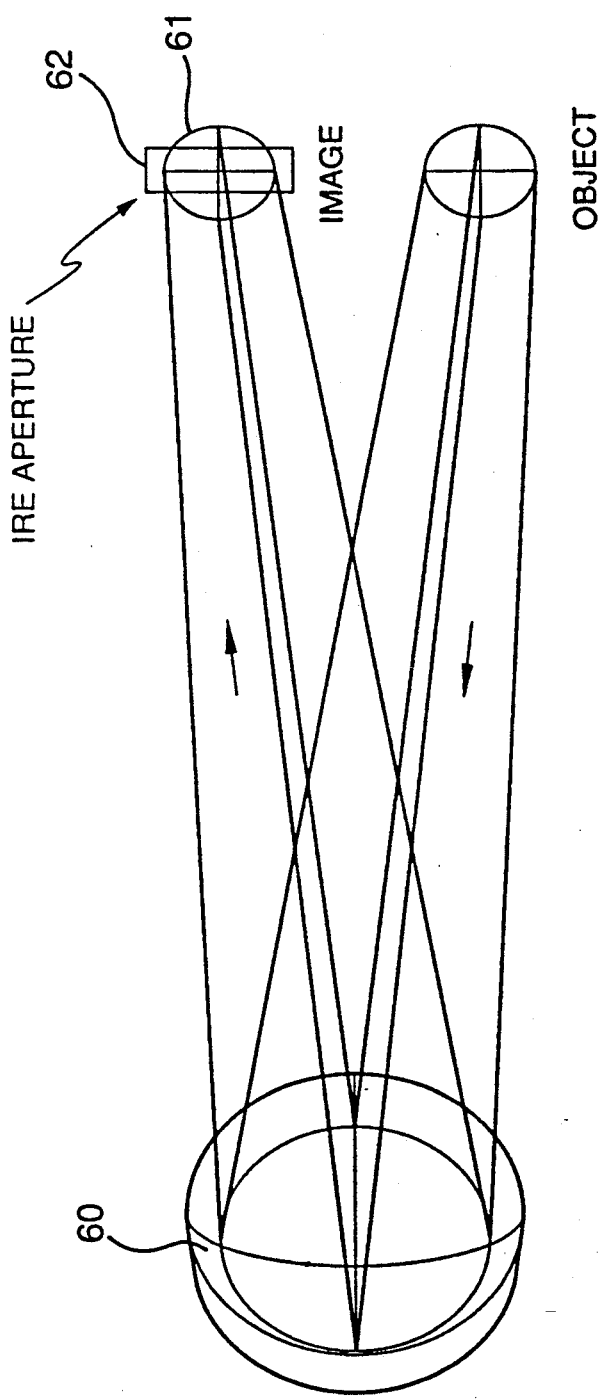
FIG. 6 illustrates the optics of a prior art arrangement but with on-axis or small off-axis angles where the problem solved by the present invention is essentially absent.

FIG. 6 illustrates a prior art device using an on-axis or small off-axis angular geometry with a spherical mirror 60. The beam 61 imaging on the rectangular IRE entrance aperture 62 doesn't match, and overfills the aperture wasting energy. For large off-axis operation with a spherical mirror, in accordance with the invention, we take advantage of the astigmatism as illustrated in FIGS. 2-5. The primary image is shown as oval and matches the aperture of the IRE. By proper choice of the off-axis angle, the secondary image occurs at the center of the IRE and the light path is such that it does not reflect from the edges. Hence, we obtain insensitive edges without costly masking of the IRE edges. A second spherical mirror recombines the first and second images as shown. The net result is a two-fold increase of the throughput of the system.

With specific reference to FIG. 1, plane mirrors M1 and M2 direct the round beam from the FT-IR spectrometer to be incident on the first spherical mirror M3. The latter focuses the beam into the IRE crystal via its entrance aperture. The radiation propagates down the length of the crystal, where it multiply interacts with the sample arranged on its horizontal sampling surface 33, and then is collected when it exits 35 via the exit aperture by the second spherical mirror M4. Mirror M4 reflects 36 the beam from plane mirror M5 to 37 plane mirror M6 and back 38 along its original path 12 to the detector of the spectrometer. The two spherical mirrors, M3 and M4, are utilized off-axis to take advantage of astigmatism to purposely distort the beam shape. Spherical mirrors employed off-axis generate two images as primary and secondary images of the round FT-IR beam. These images are elongated transverse to each other and are separated by a certain distance along the central ray, illustrated in FIG. 2. By off-axis is meant that the focus or optical axis of the spherical mirror does not fall on the optical axis of the incident beam. In the particular large off-axis case illustrated, which is not meant to be limiting, the optical axis of each spherical mirror extended about 22.5° below the optical axis of the incident beam at 19 and exiting beam 36, respectively.

The large off-axis angle, which will typically vary between 20° and 30°, preferably about 22.5°, is selected to provide the largest astigmatism with acceptable imaging. The off-axis angle is measured between the optical axes of the spherical mirror and incident beam. The object distance, the distance to the beam source, is then adjusted so that the secondary image coincides with the center of a typical long IRE 27 and the primary image coincides with its entrance aperture 42. The typical standard IRE has a length of about 50 mm, a width of about 10-20 mm, and a thickness of about 1-3 mm, providing 8, 13, or 25 reflections from the sampling surface for 3, 2, and 1 mm thick IRE plates, respectively.

Figure 2:
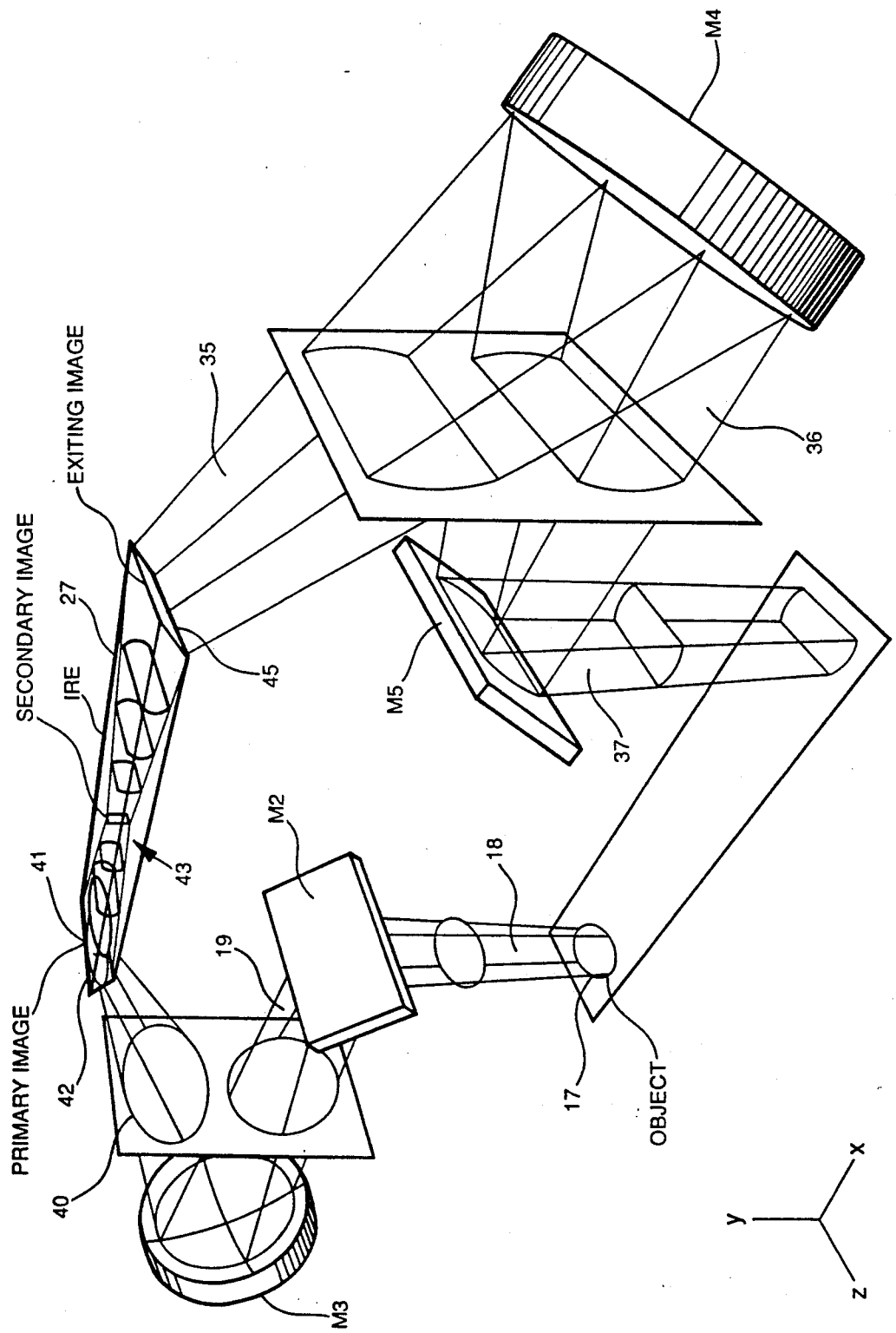
FIG. 2 is a perspective view of the optical paths through the accessory of FIG. 1.

FIG. 2 illustrates the optics involved. The object represents the incident round FT-IR beam, which is imaged on the large off-axis first spherical mirror M3. The reflected beam elongates horizontally to an oval shape 40 to form the primary image 41 at the IRE entrance aperture 42. The beam is further distorted as it propagates down the IRE plate 27 to form the transverse elongated secondary image at about the plate center at 43, and then continues to distort to produce a final generally rectangular exiting image at the plate's exiting aperture 45. The generally rectangular shape continues throughout the remaining optics until the beam is back in its original path 12.

When the IRE 27 is positioned so that its entrance aperture 42 coincides with the primary image of M3 and its width coincides with the elongated axis of the oval image 40, with the exception of some reflection losses, substantially the entire beam enters the IRE.

As the beam propagates down the length of the IRE 27, it diverges in the plane of the thickness (xz plane in FIG. 2), similar to the behaviour of a round beam focused onto the entrance aperture of an IRE. In the plane of the width of the IRE (xy plane in FIG. 2), however, the beam converges until it reaches the secondary image of M3 at 43. As the beam propagates through the remainder of the crystal 27, it diverges in both planes, filling the exit aperture 45 of the IRE. Unlike a round beam focused into an IRE, this configuration prevents the beam from striking the sides of the IRE, effectively creating optically generated insensitive edges (see U.S. Pat. No. 4,886,387 for a further elaboration of the significance of this feature). Thus, the sides of the IRE 27 may be glued into the IRE mount 26, without the losses in energy and spurious peaks associated with the adhesive.

The rectangular-shaped beam that exits the IRE 27 is collected by the second spherical mirror M4. Mirror M4 is positioned so that its secondary image coincides with the secondary image of M3 and its primary image coincides with the exit aperture 45 of the IRE. It turns out that the position of M4 is symmetrical about a vertical plane with respect to M3 as will be evident from FIG. 1. Mirror M4 thus images the beam exiting the IRE to a somewhat distorted round beam. This beam is then directed to the spectrometer detector. Since the beam 12 is then approximately the same shape and size as the beam for which the detector is configured (standard detectors have round apertures), substantially all the radiation that interacts with the sample is detected.

The accessory of the invention is a multiple reflection IR accessory with a unique solution to the problem of interfacing the round FT-IR beam to the rectangular aperture of the standard IRE. This solution provides a standard sized IRE with 8, 13, or 25 reflections on the sampling surface, and, as a bonus, it optically generates insensitive edges.

Figure 2A:
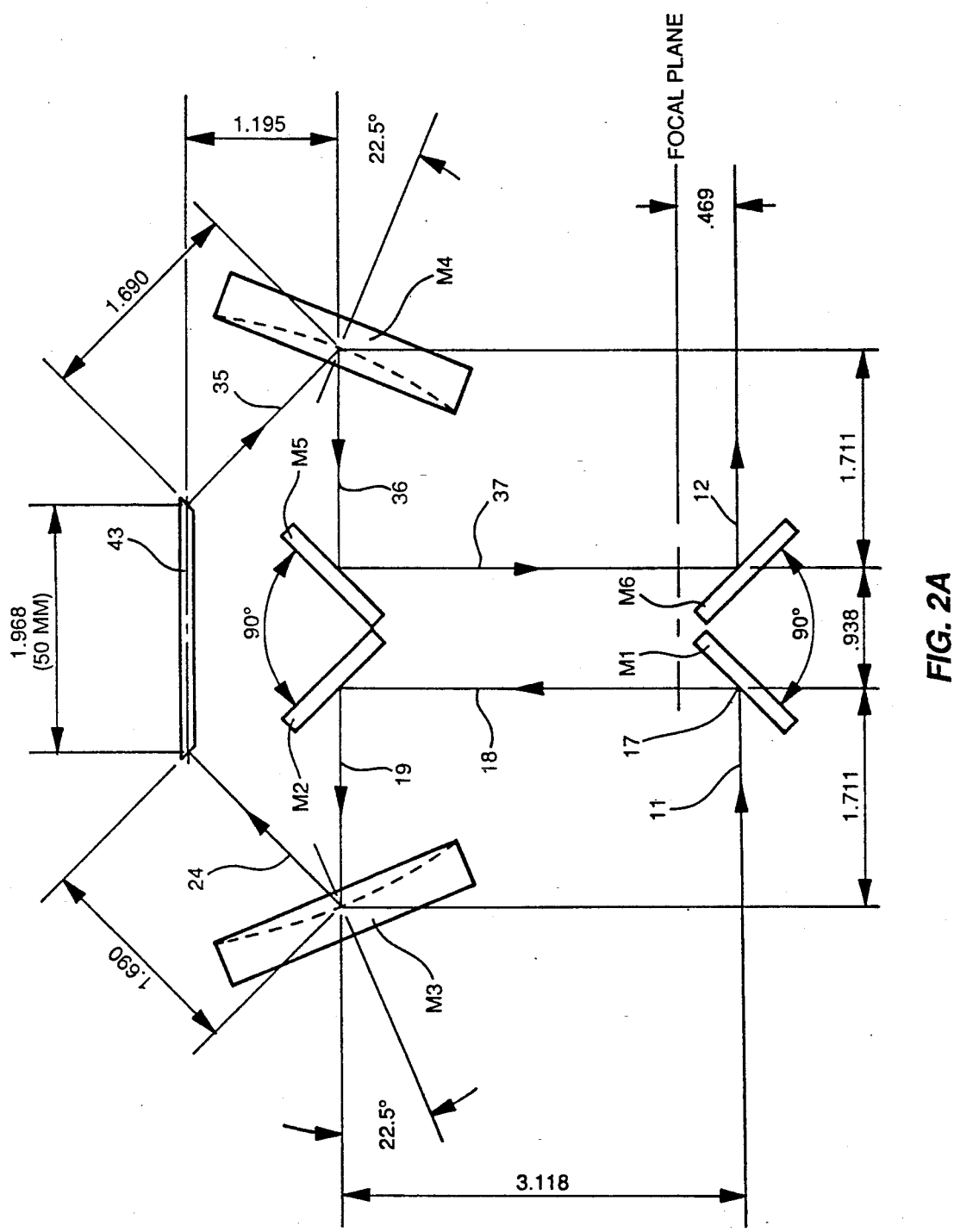
FIG. 2A depicts more clearly one form of optical layout with sample optical path dimensions.

As and example to illustrate how one skilled in the art would dimension an accessory to achieve the benefits of the invention, one accessory we built and successfully reduced to practice had the following dimensions and optical distances, reference being had to FIG. 2A. The object 17 shown in FIG. 2 is the round incident beam image on mirror M1, which had a diameter of 8 mm. Mirror M2 is located vertically above mirror M1 with the mirror centers spaced 7.92 cm apart. The mirror M2 center is spaced horizontally from the center of spherical mirror M3 1.711 cm and is located in a vertical plane, with all the other optics in the same plane, above the spherical mirror center, producing an off-axis angle of about 22.5°. The center of spherical mirror M3 was located 1.69 cm from the entranc aperture 42 of the IRE. The beam was incident orthogonally on the 45° bevelled entrance aperture and thus was incident on the top sampling surface at the same 45° angle. The geometry of mirrors M4, M5, M6 was symmetrical with the same spacings to each other and to the IRE. Other spacings can be found in FIG. 2A. With this geometry, we measured an oval beam shape of $9 \times 2.8$ mm on the $10 \times 2.8$ mm entrance aperture 42, a secondary image of 6 mm vertically at the IRE center (25 mm from the entrance aperture) and a rectangular exiting image at the exit aperture 45 of $10 \times 2.8$ mm. The beam typically will always fill the IRE exit aperture vertically, but, depending on its initial diameter, may not fill the exit aperture horizontally. Hence, the beam shape 35 at the output will be generally more squarish, though still recrangular. Typical dimensions would be $8 \times 8$–10 mm. It can be broadly characterized as squared-rectangular or generally oval. The same squared-rectangular beam shape, now converging, was transmitted to the FT-IR detector which in this case was provided with a circular aperture of about 1.3 mm diameter. This substantially matched that of the converging incident squared-rectangular beam. It will be evident that detectors with square entrance apertures could be substituted with similar results.

It will be further evident that the invention is not limited to this specific construction and other geometries achieving the benefits of the invention will be obvious to those skilled in this art following the teachings herein. The important considerations are that the dimensioning is chosen such that (a) the round object beam at 17 is transformed into a primary image having an oval shape at the rectangular IRE entrance aperture, (b) the beam is rotated 90° so that its secondary image is transverse at about the IRE center, (c) and the beam shape is rotated another 90° and thus transformed into a generally squared-rectangular shape, oriented in the same direction as the primary image, at the IRE exit aperture 45. Symmetrical positioning of the downstream optics M4, M5, M6 results in maintenance of that generally squared-rectangular beam in its path to the spectrometer detector.

Figure 3:
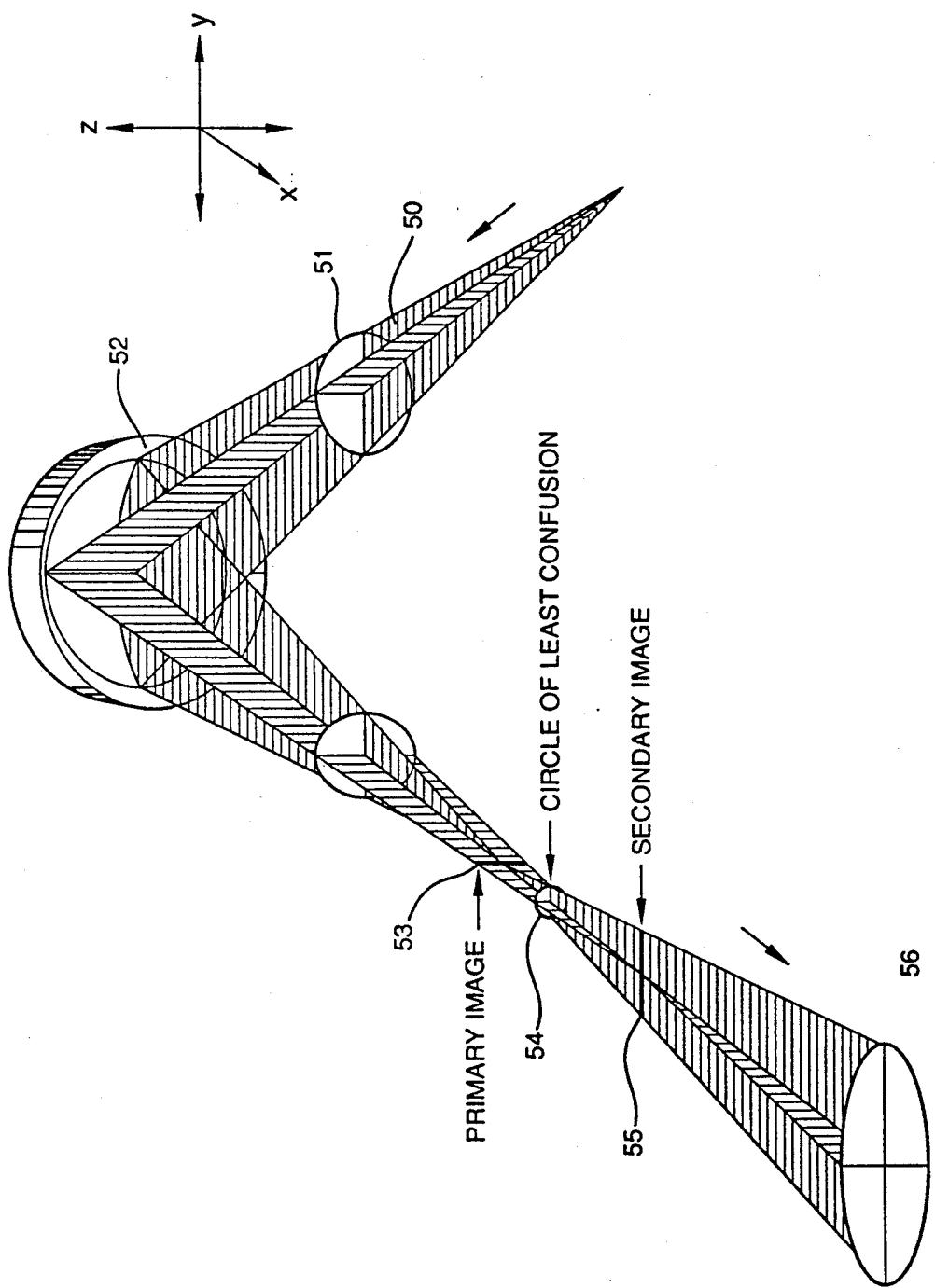
FIG. 3 schematically illustrates the optics of an off-axis spherical mirror.

FIG. 3 illustrates from a different angle the effect of a large off-axis spherical mirror on a round beam shape. The incident beam at 50, with a round cross-section 51, reflected off off-axis spherical mirror 52, forms along the reflected beam path the Z-axis elongated primary image 53, the round circle of least confusion 54, and the Y-axis elongated secondary axis 55. FIG. 4 is another view of part of FIG. 2 from the top illustrating again the effects. FIG. 5 is still another view of the different shapes the beam adopts after reflection from the large off-axis spherical mirror M3.

Figure 7:
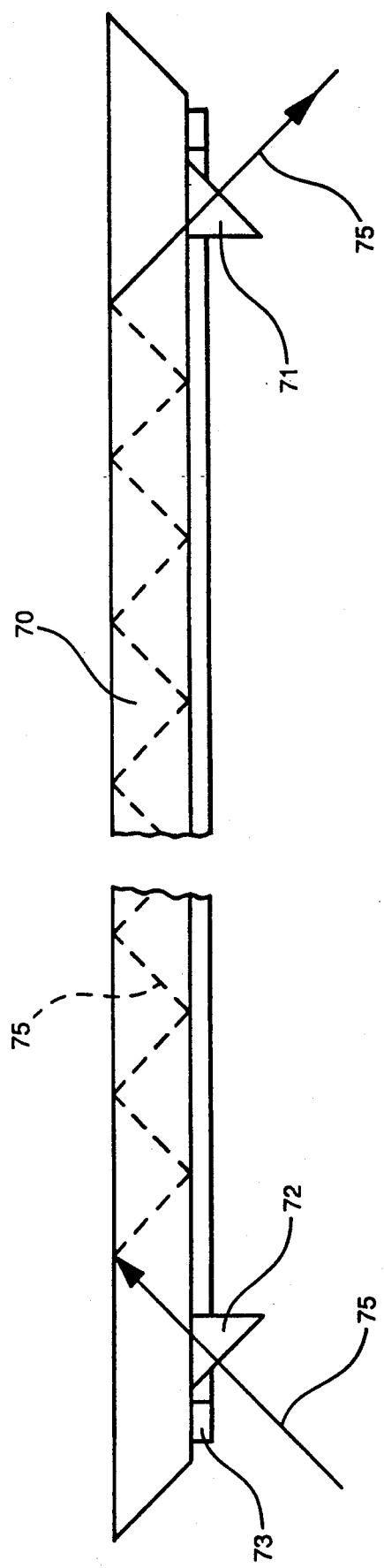
FIG. 7 is a detail view of a modified IRE plate for use in the device of FIG. 1.

FIG. 7 shows the optics of another embodiment of an accessory of the invention in which the entrance and exit apertures of the IRE plate 70, which are still rectangular, are represented by prisms 71, 72 mounted on the bottom surface of the IRE. For liquid samples, a seal 73 can be used to seal the plate 70 to the holder 26. The seal 73 and plate ends, which can be cemented to the holder opening, are not in the beam paths 75 and thus will not contribute spurious spectra.

Figure 8:
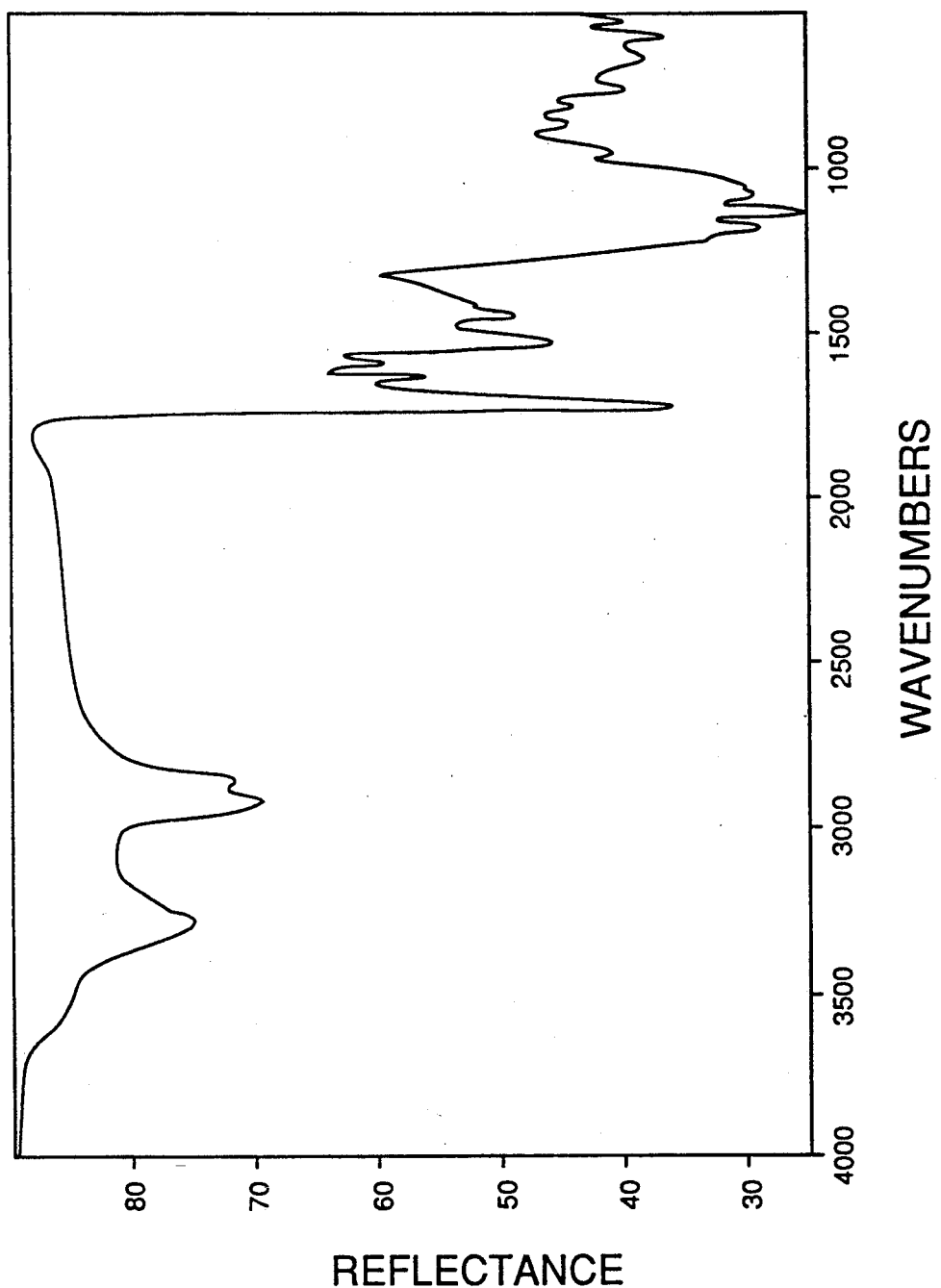
FIGS. 8–10 are spectra of various samples taken with the device of FIG. 1.
Figure 9:
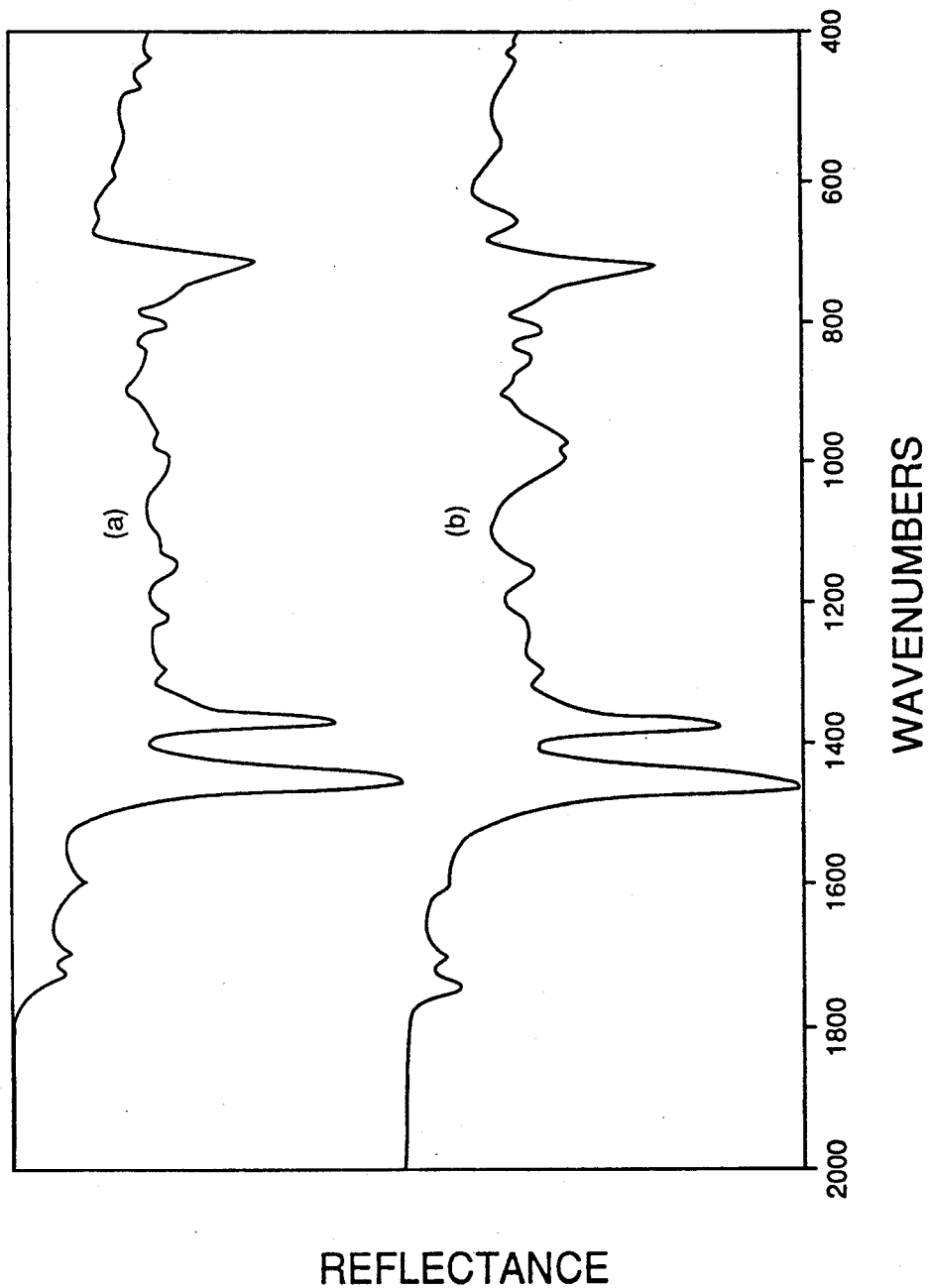
Figure 10:
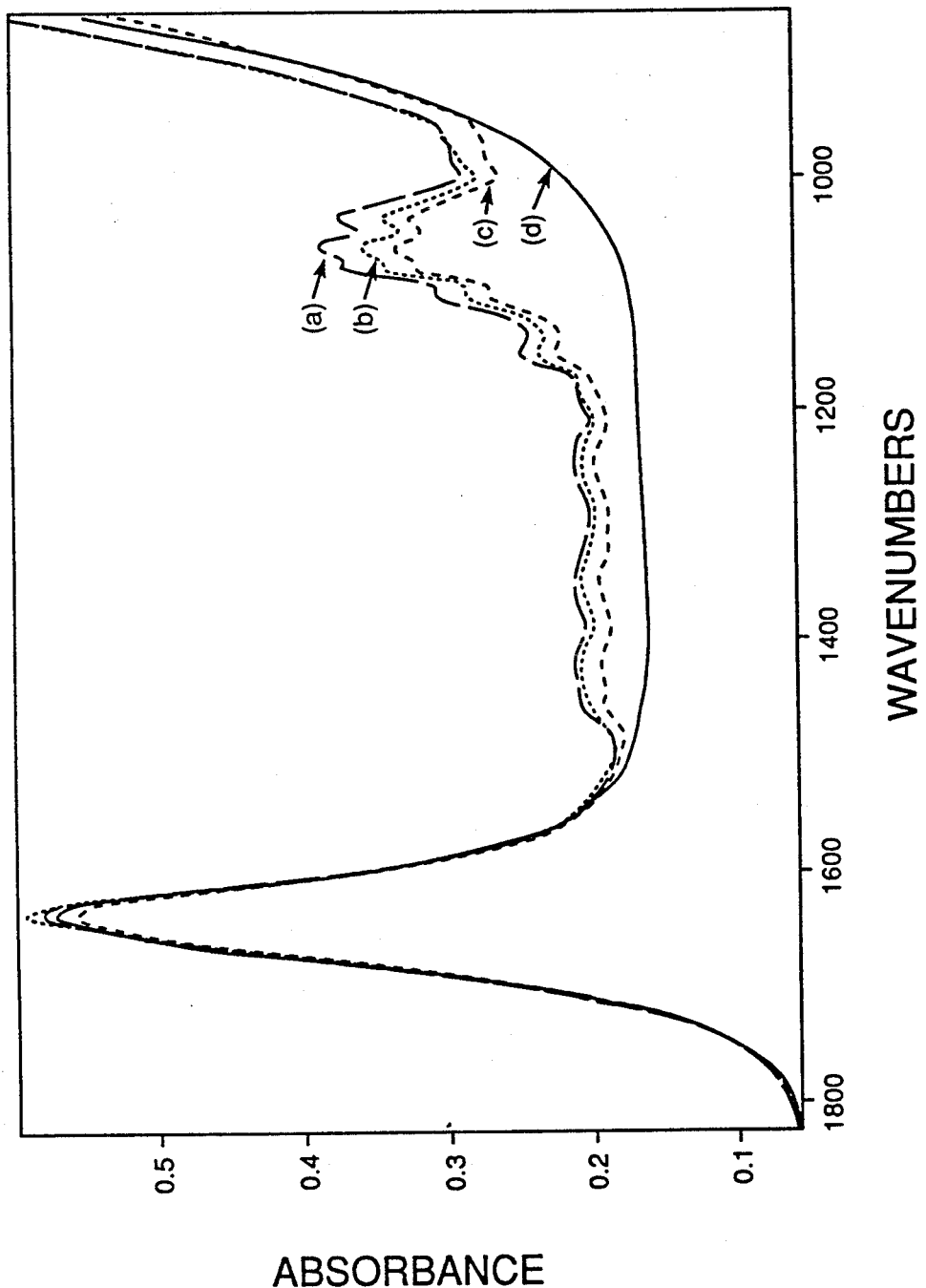

Several samples were examined to illustrate the applications of the accessories of the invention used in conjunction with a Nicolet 740 FT-IR spectrometer. The accessories of the invention generate high quality spectra of a variety of materials, as demonstrated by FIGS. 8–10. FIG. 8 is the spectra of black foam packing material pressed onto the sampling surface of the IRE. FIG. 9 is the spectra of used (a) and new (b) motor oil. FIG. 10 shows the spectra of drops on the sampling surface of 4 different commercial soft drinks, 3 of which (a–c) have absorptions due to sugar in 1000–1500 $cm^{-1}$ region, easily distinguished from the underlying broad water absorption. The fourth (d) is a diet version with no sugar. The relative sugar content is easily visible.

It will be observed that the basic optics of the FIG. 1 embodiment is symmetrical about a vertical plane passing through the center of the IRE plate 27 and between mirror pairs M2-M5 and M1-M6. Thus, the three optical elements M4, M5, and M6 for the exiting beam are a mirror image of the three optical elements M1, M2, and M3 for the entering beam. As previously indicated, the exiting beam 12 goes back into the spectrometer for detection, and the resultant electrical signal is processed in the well-known manner.

Although the accessory according to the invention is intended primarily for internal reflectance studies of solid and liquid samples, it can easily be adapted for external or in-line diffuse reflectance.

Summarizing, the multiple internal reflection accessories described here utilizes a novel approach to match the beam size and shape to the IRE aperture. Its transfer optics deliberately distort the beam entering and exiting the IRE so that the cross-section of the beam is matched to that of the standard rectangular aperture of the IRE. This configuration reduces energy losses, eliminates the need to aluminize the edges of the crystal, and reduces spurious peaks from the adhesive used to conventionally mount the crystal. It is especially useful for IRE plates mounted in a horizontal plane used for liquid and solid samples.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An accessory for internal reflection spectroscopy, comprising:
   (a) an accessory support,
   (b) an internal reflection element serving as a sample holder on said support, said internal reflection element comprising a substantially radiation transparent, parallelepiped or trapezoidal shape crystal having an exposed flat sampling surface portion for receiving a sample to be analyzed, said internal reflection element having generally rectangular entrance and exit apertures for a radiation beam,
   (c) first directing means on the support for directing an incident round beam of radiation on to the entrance aperture of the internal reflection element such that the beam internally reflects from the crystal's sampling surface portion, the internally reflected beam exiting the crystal via its exit aperture, said first directing means comprising a first spherical mirror located off-axis with respect to the optical axis of the incident beam such that the round beam shape is transformed into a generally oval shape more closely matching the shape of the rectangular entrance aperture,
   (d) second directing means on the support for receiving and redirecting the exiting reflected beam, said second directing means comprising a second spherical mirror located off-axis with respect to the optical axis of the incident beam, wherein the beam shape after being redirected by the second directing means has a distorted round shape.

2. The accessory of claim 1, wherein the first directing means includes a first plane mirror and the second directing means includes a second plane mirror.

3. The accessory of claim 2, wherein the first directing means is positioned such that the beam multiply internally reflects from the sampling surface.

4. The accessory of claim 1, wherein the off-axis angle for both the first and second spherical mirrors is about 20°–30°.

5. The accessory of claim 1, wherein the internal reflection element is transparent to infrared radiation, and the crystal has dimensions of about 50×10–20×1–3 mm.

6. The accessory of claim 1, wherein the sample holder comprises a structure having a central support for receiving the crystal with its sampling surface facing up.

7. The accessory of claim 6, further comprising pressure applying means mounted on an upper support extending over the crystal.

8. An internal reflecting spectrophotometer comprising;
   (a) a source of converging infrared radiation forming a round beam,
   (b) a sampling compartment into which the beam is received,
   (c) an internal reflection element serving as a sample holder and provided in said sampling compartment, said internal reflection element comprising a substantially infrared radiation transparent trapezoidal or parallelepiped shaped crystal having an exposed flat sampling surface portion for receiving a sample to be analyzed and means forming rectangular entrance and exit apertures for the beam,
   (d) first means in the sampling compartment for transforming the round beam into a generally oval shape substantially matching that of the crystal's entrance aperture and directing same into the entrance aperture such that the beam internally reflects from the crystal's sampling surface, the internally reflected beam exiting the crystal via its exit aperture, said first means comprising a spherical mirror positioned off-axis with respect to the beam axis and such that its primary image substantially coincides with the crystal's entrance aperture,
   (e) second means in the sample compartment for receiving the exiting beam and transmitting same in a generally squared-rectangular cross-section, said second means comprising a spherical mirror positioned off-axis with respect to the beam axis and such that its primary image substantially coincides with the crystal's exit aperture.

9. The spectrophotometer of claim 8, wherein the off-axis angle for both the first and second spherical mirrors ranges between about 20° and 30°.

10. The spectrophotometer of claim 9, wherein the spectrophotometer is an FT-IR spectrophotometer.

11. An accessory for internal reflection spectroscopy comprising:
   (a) an accessory support,
   (b) an internal reflection element serving as a sample holder on said support, said internal reflection element comprising a substantially radiation transparent, parallelepiped or trapezoidal shaped crystal having an exposed flat sampling surface portion for receiving a sample to be analyzed, said internal reflection element having generally rectangular entrance and exit apertures for a radiation beam,
   (c) first directing means on the support for directing an incident round beam of radiation on to the entrance aperture of the internal reflection element such that the beam internally reflects from the crystal's sampling surface portion, the internally reflected beam exiting the crystal via its exit aperture, said first directing means comprising a first spherical mirror located off-axis with respect to the optical axis of the incident beam such that the round beam shape is transformed into a generally oval shape more closely matching the shape of the rectangular entrance aperture,
   (d) second directing means on the support for receiving and redirecting the exiting reflected beam, said second directing means comprising a second spherical mirror located off-axis with respect to the optical axis of the incident beam, wherein the off-axis angle for both the first and second spherical mirrors is about 20°–30°.

12. The accessory of claim 11, wherein the sample holder comprises a structure having a central support for receiving the crystal with its sampling surface facing up.

13. The accessory of claim 11, further comprising pressure applying means mounted on an upper support extending over the crystal.

14. An internal reflecting spectrophotometer comprising:
   (a) a source of converging infrared radiation forming a round beam,
   (b) a sampling compartment into which the beam is received, (c) an internal reflection element serving as a sample holder and provided in said sampling compartment, said internal reflection element comprising a substantially infrared radiation transparent trapezoidal or parallelepiped shaped crystal having an exposed flat sampling surface portion for receiving a sample to be analyzed and means forming rectangular entrance and exit apertures for the beam, (d) first means in the sampling compartment for transforming the round beam into a generally oval shape substantially matching that of the crystal's entrance aperture and directing same into the entrance aperture such that the beam internally reflects from the crystal's sampling surface, said internally reflected beam exiting the crystal via its exit aperture, (e) second means in the sample compartment for receiving the exiting beam and transmitting same in a generally squared-rectangular cross-section.

15. The spectrophotometer of claim 14, wherein the first means comprises a spherical mirror positioned off-axis with respect to the beam axis and such that its primary image substantially coincides with the crystal's entrance aperture.

16. The spectrophotometer of claim 14, wherein the first means comprises a spherical mirror positioned off-axis with respect to the beam axis and such that its primary image substantially coincides with the crystal's entrance aperture and such that its secondary image substantially coincides with the crystal's center.

* * * * *